US006881853B2

(12) United States Patent
Teles et al.

(10) Patent No.: US 6,881,853 B2
(45) Date of Patent: Apr. 19, 2005

(54) METHOD FOR PRODUCING PROPYLENE OXIDE

(75) Inventors: Joaquim Henrique Teles, Otterstadt (DE); Alwin Rehfinger, Mutterstadt (DE); Anne Berg, Merksem (BE); Peter Rudolf, Ladenburg (DE); Norbert Rieber, Mannheim (DE); Peter Bassler, Viernheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/484,204
(22) PCT Filed: Jul. 18, 2002
(86) PCT No.: PCT/EP02/08022
§ 371 (c)(1),
(2), (4) Date: Jan. 20, 2004
(87) PCT Pub. No.: WO03/008401
PCT Pub. Date: Jan. 30, 2003

(65) Prior Publication Data
US 2004/0192945 A1 Sep. 30, 2004

(30) Foreign Application Priority Data
Jul. 19, 2001 (DE) .......................... 101 35 296

(51) Int. Cl.[7] .......................................... C07D 301/12
(52) U.S. Cl. ...................................... 549/531; 549/523
(58) Field of Search ................................. 549/531, 523

(56) References Cited
FOREIGN PATENT DOCUMENTS

| DE | 196 23 608 | 12/1997 |
| DE | 196 23 611 | 12/1997 |
| EP | 0 719 768 A1 * | 12/1995 |

* cited by examiner

Primary Examiner—Ba K. Trinh
(74) Attorney, Agent, or Firm—Oblon, Spivak, McClelland, Maier & Neustadt, P.C.

(57) ABSTRACT

A process for preparing propylene oxide comprises at least the following steps:
(a) propene is reacted with a hydroperoxide in a solvent in the presence of a zeolite catalyst to give a mixture (M0), where the mixture (M0) comprises propylene oxide, solvent, unreacted propene, unreacted hydroperoxide and oxygen,
(b) the propylene oxide is separated from the mixture (M0) so as to give a mixture (M1) which comprises unreacted propene and oxygen,
(c) the mixture (M1) is brought into contact with a liquid medium comprising at least a solvent to give the mixtures (M2) and (M3), where the mixture (M3) comprises part of the unreacted propene and oxygen and the mixture (M2) comprises solvent and residual propene, and
the mixture (M3) which has been separated off and comprises unreacted propene and oxygen has a ratio of oxygen to propene such that the mixture (M3) is not ignitable, and
the mixture (M2) is fed to at least one reaction of propene with hydroperoxide.

12 Claims, 2 Drawing Sheets

METHOD FOR PRODUCING PROPYLENE OXIDE

Figure 1:
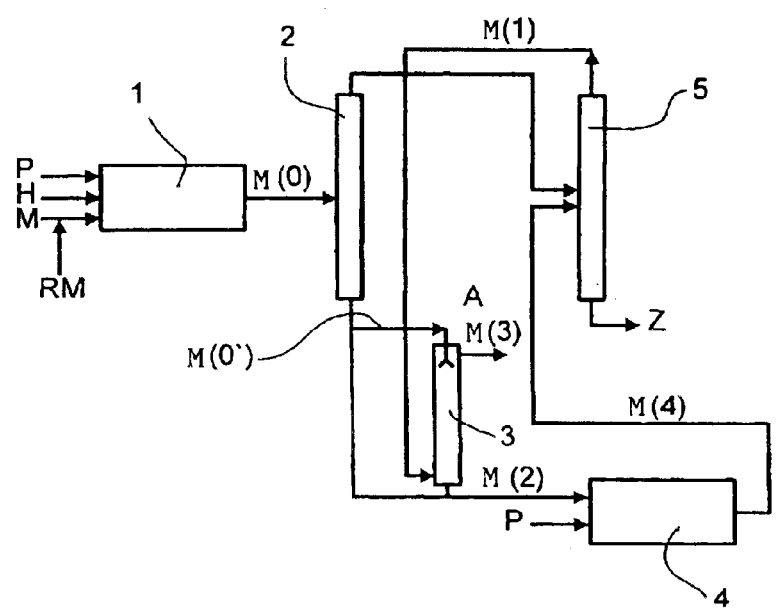

The present invention relates to a process in which propylene oxide is prepared from a hydroperoxide, preferably hydrogen peroxide, and propene, where part of the unreacted propene is recovered by means of an appropriate procedure and is returned to a reaction of propene with hydroperoxide.

In processes in which mixtures of an alkene and oxygen are obtained, it is frequently desirable to separate all or some of the alkene from this mixture and, for reasons of process economics, return it to a stage of the process. A problem which arises in such processes is the formation of ignitable mixtures which of course have to be avoided under all circumstances for safety reasons.

A process in which this problem occurs is the preparation of propylene oxide, an important intermediate in the chemical industry, from propene and hydrogen peroxide. During the work-up of the product in this process, unreacted propene is preferably separated off from the product mixture from the epoxidation and is reused as starting material in the process. When the propene is separated off from the product mixture, it is frequently accompanied by other low-boiling components which are likewise present in the product mixture, including oxygen. The oxygen is usually concentrated in the propene and reaches a concentration which leads to an ignitable mixture of propene and oxygen. This represents a safety risk in the separation process which must not be underestimated.

To solve this problem, EP-B 0 719 768 proposes carrying out the separation of propene from the low-boiling mixture in an absorption zone. In this, an inert gas, preferably methane, is introduced to such a concentration that the oxygen which is likewise present in the low-boiling mixture is diluted to a concentration at which the mixture is no longer in the ignitable range. Furthermore, this procedure requires a liquid absorption medium by means of which the propene is scrubbed from the low-boiling fraction to be fed to the absorption zone.

Accordingly, two additional components, viz. the inert gas and the liquid absorption medium, have to be used in the process just described for the epoxidation of propene using hydrogen peroxide in order to separate off or recover unreacted propene while avoiding the formation of flammable gas mixtures.

This process is therefore encumbered by increased costs and increased complication in terms of apparatus for the use of the additional components necessary in this process for safety reasons.

It is an object of the present invention to provide a process for preparing propylene oxide in which it is possible to recover at least part of the unreacted propene from a gaseous mixture comprising oxygen and unreacted propene in a simple and safe manner in order to reuse it as starting material in a stage of the process.

We have found that this object is achieved by a process for preparing propylene oxide, which comprises at least the following steps:

(a) propene is reacted with a hydroperoxide in a solvent in the presence of a zeolite catalyst to give a mixture (M0), where the mixture (M0) comprises propylene oxide, solvent, unreacted propene, unreacted hydroperoxide and oxygen, (b) the propylene oxide is separated from the mixture (M0) so as to give a mixture (M1) which comprises unreacted propene and oxygen, (c) the mixture (M1) is brought into contact with a liquid medium comprising at least a solvent to give the mixtures (M2) and (M3), where the mixture (M3) comprises part of the unreacted propene and oxygen and the mixture (M2) comprises solvent and residual propene, and the mixture (M3) which has been separated off and comprises unreacted propene and oxygen has a ratio of oxygen to propene such that the mixture (M3) is not ignitable, and the mixture (M2) is fed to at least one reaction of propene with hydroperoxide.

The separation of a mixture into at least two fractions can, for the purposes of the invention, in principle be carried out by all suitable methods.

For the purposes of the present invention, the separation of an essentially liquid mixture is preferably achieved by means of at least one distillation column.

On the other hand, the complete or partial separation of at least one gaseous component from an essentially gaseous mixture is, for the purposes of the present invention, preferably carried out using an "absorption column".

In this, the essentially gaseous mixture flowing through the column is scrubbed, generally in countercurrent, with a liquid medium (absorption medium), so that the desired gas component is absorbed completely or partially by the absorption medium and leaves the column together with the absorption medium. The gas component(s) which has/have not been absorbed can leave the column via a further suitable device.

In the process of the present invention, the desired gas component to be absorbed by the liquid medium is propene. The amount of propene which is absorbed by the liquid medium (absorption medium) during scrubbing of the gas can be controlled via all parameters which appear suitable for this purpose to a person skilled in the art, for example via the amount of absorption medium or the pressure in the absorption column which is in a range from 0.5 to 3 bar, preferably in the vicinity of atmospheric pressure. Control via the temperature prevailing in the absorption column, which is in the range from 0 to 60° C., preferably in the range from 25 to 40° C., is also possible.

For the purposes of the invention, the parameter used for controlling the amount of propene which is absorbed by the liquid medium (absorption medium) during scrubbing of the gas is preferably the amount of absorption medium used.

Preference is given to only part of the propene present in a gaseous mixture, known as the residual propene, being absorbed by the absorption medium in the absorption column or columns, so that propene is still present in the gaseous mixture remaining after the scrubbing step.

The liquid medium (absorption medium) used for absorption in the process of the present invention can in principle be any liquid medium suitable for the absorption of propene. Such media include, for example, all solvents which are known to those skilled in the art and are suitable for this purpose. Accordingly, it is possible to use, for example, the following solvents as absorption media:

water, alcohols, preferably lower alcohols, more preferably alcohols having less than 6 carbon atoms, for example methanol, ethanol, propanols, butanols, pentanols, diols or polyols, preferably those having less than 6 carbon atoms, ethers such as diethyl ether, tetrahydrofuran, dioxane, 1,2-diethoxyethane, 2-methoxyethanol, esters such as methyl acetate or butyrolactone, amides such as dimethylformamide, dimethylacetamide, N-methylpyrrolidone, ketones such as acetone, nitriles such as acetonitrile or mixtures of two or more of the compounds mentioned.

The absorption medium used for the purposes of the invention is preferably a liquid medium arising from a preceding process step. This has to be able to absorb at least part of the unreacted propene from the gaseous mixture (M1) with which it is brought into contact in the absorption column during scrubbing of the gas. The liquid medium in question particularly preferably comprises at least one solvent used in the process of the present invention.

For the purposes of the invention, the mixture (M1) comprising unreacted propene and oxygen is, in step (c), brought into contact with a liquid medium (absorption medium) comprising at least a solvent to give the mixtures (M2) and (M3).

In this process step, unreacted propene is removed from the mixture (M1) by the absorption medium and is subsequently returned to the process of the present invention. The amount of unreacted propene removed in this step is limited by the requirement that the mixture (M3), which remains, must not become ignitable.

Furthermore, it is important from a safety point of view that the mixture (M3) which leaves the absorption column via a suitable outlet facility and comprises the propene which has not been absorbed by the absorption medium together with oxygen has a ratio of oxygen to propene and any further combustible components present in (M3) which is such that the mixture (M3) is not ignitable.

For the purposes of the present invention, the term "not ignitable" means that the composition of the mixture (M3) has to be chosen so that it lies outside the ignition limits (outside the ignitable range) under the process conditions under which it is separated off, so that the mixture (M3) can be handled without it igniting. According to the definition of the Berufsgenossenschaft Chemie BGR 104 part 1 explosion protection regulations, section B, item 9, the term "ignitable mixture" refers to "a mixture of gases and vapors with one another or with mists or dusts in which ignition results in a self-propagating reaction".

Basically, the ignition limits are the lower and upper limiting concentrations of a combustible gas or vapor in admixture with air (or another oxygen-containing gas) between which the gas (vapor)/air mixture can be ignited by heating (ignition temperature) or by means of a spark. The ignition limits are dependent on pressure and temperature. They are specified as concentration of the combustible gas, vapor or oxygen in % by volume or $g/m^3$ for an initial state of 1 013 mbar and 20° C.

The ignition limits of a mixture depend essentially on the composition of its main components. Listings which may be mentioned by way of example of safety parameters of combustible gases and vapors may be found in the following reference works: Coward & Jones, US Bureau of Mines Bull. 503 (1952); Nabert & Schön, Sicherheitstechnische Kennzahlen brennbarer Gase und Dämpfe, Deutscher Eichverlag, Braunschweig (1963).

The present invention therefore also provides a process as described above in which the concentration of oxygen in the mixture (M3) is less than 12% by volume, preferably less than 11% by volume, particularly preferably less than 10% by volume.

For the purposes of the present invention, it is of course also possible to use propene containing up to 10% by weight of hydrocarbons other than propene.

For example, the propene used can contain up to 10% by weight of propane, ethane, ethylene, butane or butenes, either individually or as a mixture of two or more thereof.

Accordingly, the present invention also provides a process as described above in which the propene used contains up to 10% by weight of other hydrocarbons.

Step (a) of the above described process of the present invention is generally carried out in a main reactor (1), preferably a shell-and-tube reactor. For the purposes of the invention, it is advantageous for the molar ratio of propene to hydroperoxide in step (a) of the process of the present invention to be in a range from 0.85 to 5, preferably from 0.9 to 2, particularly preferably from 0.9 to 1.2.

In principle, all hydroperoxides known to those skilled in the art can be used for the purposes of the present invention. Details regarding the preparation of hydroperoxides or the preferred hydroperoxides may be found in DE-A 19835907.1.

However, the process of the present invention is preferably carried out using hydrogen peroxide as hydroperoxide.

Furthermore, the conversion of hydrogen peroxide in step (a) is preferably in a range from 70 to 99%, preferably in a range from 75 to 98%, particularly preferably in a range from 80 to 95%.

Accordingly, the present invention also provides a process as described above in which the hydroperoxide is hydrogen peroxide and the conversion of hydrogen peroxide in step (a) is in the range from 80 to 95%.

For the purposes of the present invention, it is in principle possible to use all solvents which appear suitable to a person skilled in the art. For example, solvents used may be water, alcohols, preferably lower alcohols, more preferably alcohols having less than 6 carbon atoms, for example methanol, ethanol, propanols, butanols, pentanols, diols or polyols, preferably those having less than 6 carbon atoms, ethers such as diethyl ether, tetrahydrofuran, dioxane, 1,2-diethoxyethane, 2-methoxyethanol, esters such as methyl acetate or butyrolactone, amides such as dimethylformamide, dimethylacetamide, N-methylpyrrolidone, ketones such as acetone, nitriles such as acetonitrile or mixtures of two or more of the compounds mentioned.

Methanol is preferably used as solvent for the purposes of the invention.

As zeolite catalysts in step (a) of the process of the present invention, it is in principle possible to use all zeolite catalysts known to those skilled in the art for such a reaction.

Preference is given to using zeolites in which iron, titanium, vanadium, chromium, niobium or zirconium is present.

Specific examples are titanium-, germanium-, tellurium-, vanadium-, chromium-, niobium- or zirconium-containing zeolites having a pentasil zeolite structure, in particular the types which are assigned on the basis of their X-ray diffraction patterns to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNL VSV, WIE, WEN, YUG, ZON structures and to mixed structures derived from two or more of the abovementioned structures. It is also conceivable for further titanium-containing zeolites having the structure ITQ-4, SSZ-24, TTM-1, UTD-1, CIT-1 or CIT-5 to be used in the process of the present invention. Further titanium-containing zeolites which may be mentioned are those having the ZSM-48 or ZSM-12 structure.

In the process of the present invention, preference is given to using Ti zeolites having an MFI, MEL or mixed MFI/MEL structure. Further specific examples of preferred zeolites are the Ti-containing zeolite catalysts which are generally referred to as "TS-1", "TS-2", "TS-3", and also Ti zeolites having a framework structure isomorphous with β-zeolite.

The present invention therefore also provides a process as described above in which the zeolite catalyst is a titanium silicalite catalyst, in particular a titanium silicalite catalyst having the TS-1 structure.

Further details regarding the catalysts which can be used, in particular zeolites, may be found in DE-A 1010139.2.

The mixture (M0) arising from step (a) consists essentially of the following components: propylene oxide as desired process product, solvent, unreacted propene, unreacted hydroperoxide and oxygen.

Further components which may be present in the mixture (M0) are water and, depending on the propane or hydrocarbon content of the propene used, propane and further hydrocarbons, where the compounds referred to as "hydrocarbons" are of course different from propene.

In a further step (b), propylene oxide is separated from the mixture (M0) resulting from step (a) of the process of the present invention so as to give a mixture (M1) comprising unreacted propene and oxygen.

The separation of propylene oxide from the mixture (M0) and the further work-up of the other components present in (M0) is, for the purposes of the present invention, preferably carried out according to one of the following two process variants, viz. variant 1 and variant 2.

These two variants, which are schematically shown in FIG. 1 (variant 1) and FIG. 2 (variant 2), are described in detail below.

Variant 1:

A preferred method (variant 1, FIG. 1) of separating off the propylene oxide comprises fractionating the product mixture from the main reactor (1) in a column (2) which directly follows the main reactor (1) to give a top fraction and a bottom fraction. The bottom fraction from the column (2), viz. mixture (M0'), comprises solvent, unreacted hydroperoxide and water. The top fraction from this column (2) comprises mostly propylene oxide, unreacted propene and oxygen and is passed to a further column (5).

The top fraction from this column (2) may further comprise small amounts of solvent. In the process of the present invention, the top fraction from the column (2) preferably contains less than 60% by weight, particularly preferably less than 50% by weight, of solvent.

In column (5), the propylene oxide is taken off via the bottom fraction and, if appropriate, subjected to further work-up steps in which the propylene oxide is separated off from the further components present in the bottom fraction, e.g. solvent and water, and purified.

In the work-up of the bottom fraction from column (5), it is also possible to recover the solvent and reuse it in the process. The recovered solvent is preferably returned to step (a).

The top fraction from the column (5), viz. the mixture (M1), consists essentially of unreacted propene and oxygen and is passed to the absorption column (3) for further work-up.

In the absorption column (3), the gaseous mixture (M1) is scrubbed with part or all of the mixture (M0'), viz. the liquid bottom fraction from the column (2). Here, the mixture (M0') or part thereof, which comprises solvent, unreacted hydroperoxide and water, serves as absorption medium for part of the unreacted propene present in the mixture (M1).

In the process of the present invention, the amount of unreacted propene separated from the mixture (M1) can be controlled via the amount of liquid mixture (M0') used for scrubbing the gaseous mixture (M1).

The amount of the mixture (M0') is preferably set by means of appropriate control systems known to those skilled in the art, which may comprise, for example, at least one bypass or valve system.

Thus, mixture (M0') can, if required, be divided into two or more fractions. Preference is given to using at least one of these fractions in the absorption column as absorption medium (liquid medium) for scrubbing the gaseous mixture (M1).

The fraction of the mixture (M0') which is not fed to the absorption column can be combined, in its entirety or in part, with the liquid mixture leaving the absorption column (3), in which the part of the propene absorbed from mixture (M1) in the gas scrubbing step (residual propene) is present, to give a mixture (M2).

The scrubbing of the gas in the absorption column (3) thus removes part of the unreacted propene from the mixture (M1). Accordingly, the mixture (M2) coming from this process step comprises residual propene and the components of the absorption medium, solvent, water and unreacted hydrogen peroxide.

The gaseous mixture (M3) which likewise comes from this process step and leaves the absorption column (3) through its own outlet device therefore comprises the part of the unreacted propene which is not absorbed, together with oxygen.

The conditions in the absorption column (3) have to be chosen so that unreacted propene and oxygen are present in the gaseous mixture (M3) leaving the absorption column (3) in such a ratio that the mixture is not ignitable.

Furthermore, it is also possible for small amounts of other volatile components to be present in addition to unreacted propene and oxygen in the mixture (M3).

The mixture (M2) is fed to at least one further reaction of propene with hydroperoxide in an after-reactor (4), preferably a shell-and-tube reactor.

In the after-reactor (4), mixture (M2) is once again admixed with such an amount of propene that the unreacted hydroperoxide still present in the mixture (M2) is almost completely reacted with propene to form propylene oxide, giving a mixture (M4).

The crude output from the after-reactor (4) accordingly comprises propylene oxide, solvent, water, unreacted propene and less than 500 ppm of unreacted hydroperoxide.

The mixture (M4) can subsequently be worked up further to separate off the desired product propylene oxide. All or part of this work-up can in principle be carried out in a further procedure separate from the process described above.

However, for the purposes of the present invention, the mixture (M4) is preferably transferred in its entirety to column (5) and there combined with the top fraction from column (2).

The mixture in column (5) is processed as described above.

Accordingly, the present invention also provides a process as described above in which the mixture (M2) further comprises hydroperoxide and is, in the further steps (d) and (e) following the step (c), fed to a reaction of propene with hydroperoxide, as follows:

(d) the mixture (M2) is admixed with further propene so that the propene reacts with most of the unreacted hydroperoxide present in the mixture (M2) to form propylene oxide, giving a mixture (M4), and (e) the mixture (M4) is returned to the separation of step (b).

Variant 2:

A further preferred method (variant 2, FIG. 2) of separating propylene oxide from the product mixture from the main reactor (1) comprises transferring the product mixture into a column (6) which directly follows the main reactor (1) and in which the mixture (M0) is separated into a top fraction and a bottom fraction.

The bottom fraction from column (6), which comprises propylene oxide, solvent and unreacted hydroperoxide and water, is passed to further work-up steps to work it up further and separate off the propylene oxide.

The solvent present in this bottom fraction is recovered in the course of the work-up.

The top fraction from column (6), viz. the mixture (M1), consists essentially of unreacted propene and oxygen.

Mixture (M1) is transferred into the subsequent absorption column (7). In this, the gaseous mixture (M1) is scrubbed with all or part of the solvent recovered from the bottom fraction from column (6) so as to give a gaseous mixture (M3) and a liquid mixture (M2). Consequently, the recovered solvent serves as absorption medium for the unreacted propene present in mixture (M1) in this variant of the process.

The gaseous mixture (M3) comprises oxygen together with the part of the unreacted propene in mixture (M1) which has not been absorbed by the solvent. The liquid mixture (M2) accordingly comprises the solvent together with the propene which it has absorbed (residual propene).

In this variant of the process of the present invention, the amount of propene which is absorbed by the absorption medium during scrubbing of the gaseous mixture (M1) can thus be controlled via the amount of solvent which is used as absorption medium in the absorption column (7).

In this process step, unreacted propene is removed from the mixture (M1) by means of the absorption medium and is subsequently returned to the process of the present invention. The amount of unreacted propene removed in this step is limited by the requirement that the remaining mixture (M3) must not become ignitable.

The conditions in the absorption column (7) are therefore chosen so that the propene-and-oxygen containing mixture (M3) which leaves the absorption column via its own outlet facility is not ignitable.

Mixture (M2) is discharged from the absorption column, if appropriate worked up, and then returned to step (a) of the process.

In the process of the present invention, the mixture (M2) is worked up if appropriate and returned to step (a) of the process.

The present invention therefore also provides a process as described above in which the mixture (M2) is fed to a reaction of propene with hydroperoxide in a further step (f) following step (c), as follows:

(f) the mixture (M2) is worked up if appropriate and returned to step (a).

List of Reference Numerals

FIG. 1: 1 Main reactor (1)
2 Column (2)
3 Absorption column (3)
4 After-reactor (4)
5 Column (5)

Figure 2:
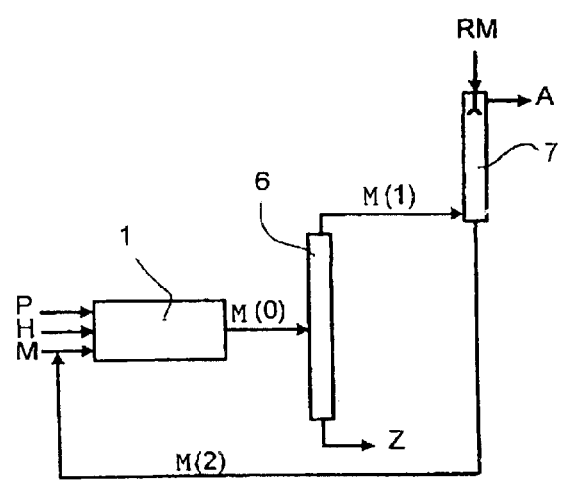

FIG. 2: 1 Main reactor (1)
6 Column (6)
7 Absorption column (7)

List of abbreviations
P: Propene
H: $H_2O_2$
M: Methanol
RM: Recycled methanol from work-up
A: Offgas
Z: To further work-up

We claim:

1. A process for preparing propylene oxide, which comprises at least the following steps:

(a) propene is reacted with a hydroperoxide in a solvent in the presence of a zeolite catalyst to give a mixture (M0), where the mixture (M0) comprises propylene oxide, solvent, unreacted propene, unreacted hydroperoxide and oxygen, (b) the propylene oxide is separated from the mixture (M0) so as to give a mixture (M1) which comprises unreacted propene and oxygen, (c) the mixture (M1) is brought into contact with a liquid medium comprising at least a solvent to give the mixtures (M2) and (M3), where the mixture (M3) comprises part of the unreacted propene and oxygen and the mixture (M2) comprises solvent and residual propene, and where the mixture (M3) which has been separated off and comprises unreacted propene and oxygen has a ratio of oxygen to propene such that the mixture (M3) is not ignitable, and where the mixture (M2) is fed to at least one reaction of propene with hydroperoxide.

2. The process as claimed in claim 1, wherein the concentration of oxygen in the mixture (M3) is less than 12% by volume.

3. The process as claimed in claim 1, wherein the mixture (M2) further comprises hydroperoxide and is, in the further steps (d) and (e) following the step (c), fed to a reaction of propene with hydroperoxide, as follows:

(d) the mixture (M2) is admixed with further propene so that the propene reacts with most of the unreacted hydroperoxide present in the mixture (M2) to form propylene oxide, giving a mixture (M4), and (e) the mixture (M4) is returned physically to the separation of step (b).

4. The process as claimed in claim 1, wherein the mixture (M2) is fed to a reaction of propene with hydroperoxide in a further step (f) following step (c), as follows:

(f) the mixture (M2) is worked up if appropriate and returned to step (a).

5. The process as claimed in claim 1, wherein the hydroperoxide is hydrogen peroxide and the conversion of hydrogen peroxide in (a) is in the range from 80 to 95%.

6. The process as claimed in claim 1, wherein the zeolite catalyst is a titanium silicalite catalyst.

7. The process as claimed in claim 1, wherein the propene used contains up to 10% by weight of other hydrocarbons.

8. A process for preparing propylene oxide, which comprises at least the following steps:

(a) propene is reacted with a hydroperoxide in a solvent in the presence of a zeolite catalyst to give a mixture (M0), where the mixture (M0) comprises propylene oxide, solvent, unreacted propene, unreacted hydroperoxide and oxygen, (b) the propylene oxide is separated from the mixture (M0) so as to give a mixture (M1) which comprises unreacted propene and oxygen, (c) the mixture (M1) is brought into contact with a liquid medium comprising at least a solvent to give the mixtures (M2) and (M3), where the mixture (M3) comprises part of the unreacted propene and oxygen and the mixture (M2) comprises solvent, hydroperoxide and residual propene, (d) the mixture (M2) is admixed with further propene so that the propene reacts with most of the unreacted hydroperoxide present in the mixture (M2) to form propylene oxide, giving a mixture (M4), and (e) the mixture (M4) is returned physically to the separation of step (b), and where the mixture (M3) which has been separated off and comprises unreacted propene and oxygen has a ratio of oxygen to propene such that the mixture (M3) is not ignitable.

9. The process as claimed in claim 8, wherein the concentration of oxygen in the mixture (M3) is less than 12% by volume, and wherein the propene used contains up to 10% by weight of other hydrocarbons.

10. A process for preparing propylene oxide, which comprises at least the following steps:

(a) propene is reacted with a hydroperoxide in a solvent in the presence of a zeolite catalyst to give a mixture (M0), where the mixture (M0) comprises propylene oxide, solvent, unreacted propene, unreacted hydroperoxide and oxygen, (b) the propylene oxide is separated from the mixture (M0) so as to give a mixture (M1) which comprises unreacted propene and oxygen, (c) the mixture (M1) is brought into contact with a liquid medium comprising at least a solvent to give the mixtures (M2) and (M3), where the mixture (M3) comprises part of the unreacted propene and oxygen and the mixture (M2) comprises solvent and residual propene, and (d) the mixture (M2) is worked up if appropriate and returned to step (a), and where the mixture (M3) which has been separated off and comprises unreacted, propene and oxygen has a ratio of oxygen to propene such that the mixture (M3) is not ignitable.

11. The process as claimed in claim 10, wherein the concentration of oxygen in the mixture (m3) is less than 12% by volume, and wherein the propene used contains up to 10% by weight of other hydrocarbons.

12. The process as claimed in claim 6, wherein the titanium silicalite catalyst has a TS-1 structure.

* * * * *